United States Patent
Warner et al.

(10) Patent No.: US 9,717,567 B1
(45) Date of Patent: *Aug. 1, 2017

(54) TEAR-RESISTANT DENTAL DAMS

(71) Applicant: Easydam, LLC, Rochester Hills, MI (US)

(72) Inventors: Thomas P. Warner, Rochester Hills, MI (US); Allan Kotwicki, Williamsburg, MI (US)

(73) Assignee: Easydam, LLC, Rochester Hills, MI (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/744,589

(22) Filed: Jun. 19, 2015

Related U.S. Application Data

(63) Continuation of application No. 13/832,089, filed on Mar. 15, 2013, now Pat. No. 9,060,830.

(51) Int. Cl.
*A61C 5/14* (2006.01)
*A61C 5/12* (2006.01)

(52) U.S. Cl.
CPC .................. *A61C 5/122* (2013.01)

(58) Field of Classification Search
CPC ........................................................ A61C 5/122
USPC ................................................... 433/38, 136
See application file for complete search history.

(56) References Cited

U.S. PATENT DOCUMENTS

| | | | | |
|---|---|---|---|---|
| 2,275,425 A | * | 3/1942 | Grabec | B44C 1/16 156/220 |
| 6,830,800 B2 | * | 12/2004 | Curro | A47L 1/15 428/131 |
| 2005/0106533 A1 | * | 5/2005 | Mannschedel | A61C 5/122 433/136 |

* cited by examiner

*Primary Examiner* — Pedro Philogene
*Assistant Examiner* — David C Comstock
(74) *Attorney, Agent, or Firm* — Buckert Patent & Trademark Law Firm PC; John F. Buckert

(57) ABSTRACT

A tear-resistant dental dam is provided. The tear-resistant dental dam includes a first thermoplastic elastomeric sheet and a second thermoplastic elastomeric sheet disposed on the first thermoplastic elastomeric sheet. The first and second thermoplastic elastomeric sheets have a grid pattern of weld joint regions configured to couple together the first and second thermoplastic elastomeric sheets. The grid pattern of weld joint regions define a plurality of unwelded regions of the first and second thermoplastic elastomeric sheets.

16 Claims, 12 Drawing Sheets

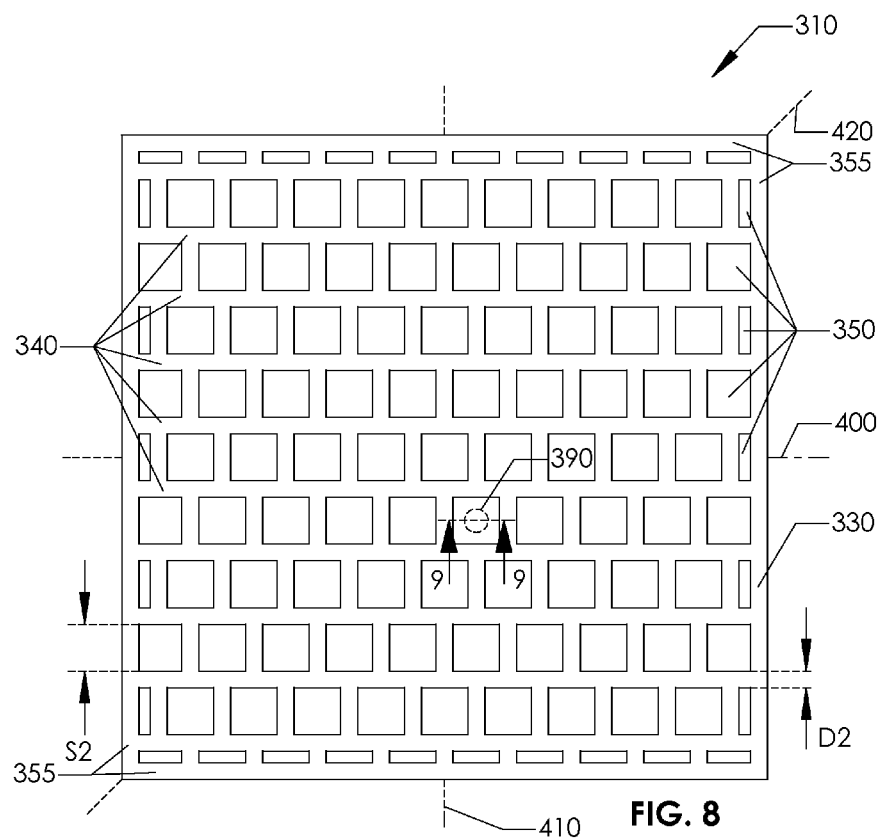
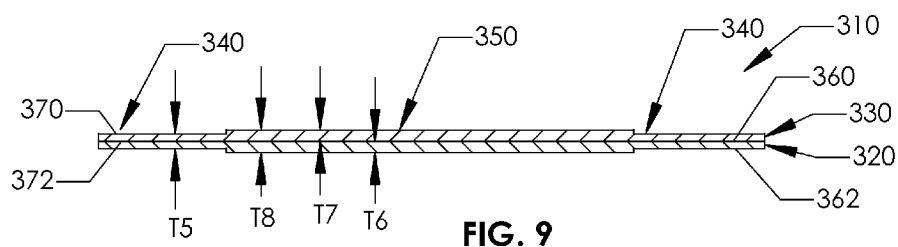

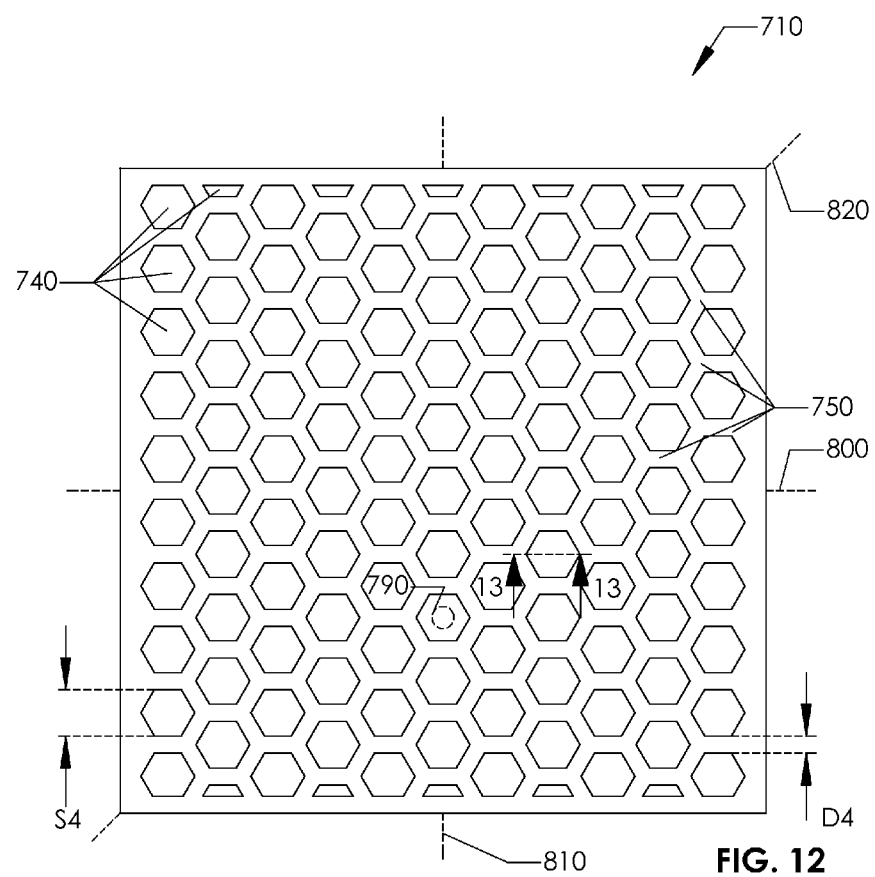
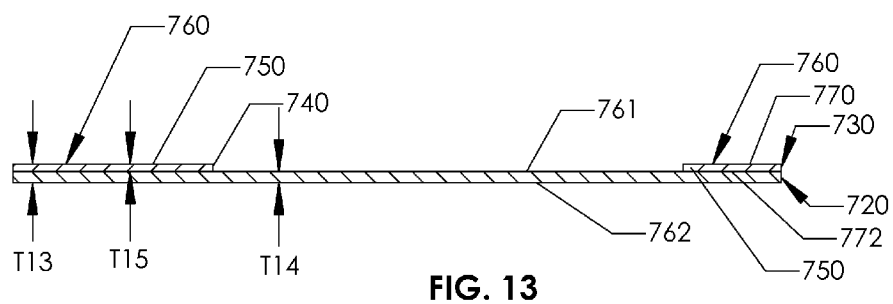

TEAR-RESISTANT DENTAL DAMS

CROSS-REFERENCE TO RELATED APPLICATIONS

This application is a continuation of U.S. patent application Ser. No. 13/832,089 filed on Mar. 15, 2013, the entire contents of which are hereby incorporated by reference herein.

BACKGROUND

Dental dams are utilized in many dental procedures including root canal procedures. The problem associated with a dental dam is that a dental instrument or tension on the dental dam can easily tear the dental dam and thereafter the tear typically propagates across a substantial length of the dental dam. As result, the dentist must replace the torn dental dam which results in wasted time, a wasted dental dam, and increased dental patient expense associated with the dental procedure.

The inventors herein recognized the need for an improved dental dam that eliminates and/or minimizes the above mentioned deficiency.

SUMMARY

A tear-resistant dental dam in accordance with an exemplary embodiment is provided. The tear-resistant dental dam includes a first elastomeric sheet and a second elastomeric sheet disposed on the first elastomeric sheet. The first and second elastomeric sheets have a grid pattern of weld joint regions configured to couple together the first and second elastomeric sheets. The grid pattern of weld joint regions define a plurality of unwelded regions of the first and second elastomeric sheets.

A tear-resistant dental dam in accordance with another exemplary embodiment is provided. The tear-resistant dental dam includes a first elastomeric sheet and a second elastomeric sheet disposed on the first elastomeric sheet. The second elastomeric sheet has a plurality of apertures extending therethrough that define a grid pattern of elastomeric material of the second elastomeric sheet. The grid pattern of elastomeric material is coupled to the first elastomeric sheet.

A tear-resistant dental dam in accordance with another exemplary embodiment is provided. The tear-resistant dental dam includes an elastomeric sheet having a plurality of pocket regions defining a grid pattern of elastomeric material. A thickness of a portion of the elastomeric sheet underlying the plurality of pocket regions is less than a thickness of the grid pattern of elastomeric material.

BRIEF DESCRIPTION OF THE DRAWINGS

FIG. 8 is a schematic of a tear-resistant dental dam in accordance with another exemplary embodiment;

FIG. 9 is a cross-sectional schematic of a portion of the tear-resistant dental dam of FIG. 8;

FIG. 12 is a schematic of a tear-resistant dental dam in accordance with another exemplary embodiment;

FIG. 13 is a cross-sectional schematic of a portion of the tear-resistant dental dam of FIG. 12;

DETAILED DESCRIPTION

First Dental Dam Embodiment

Figure 1:
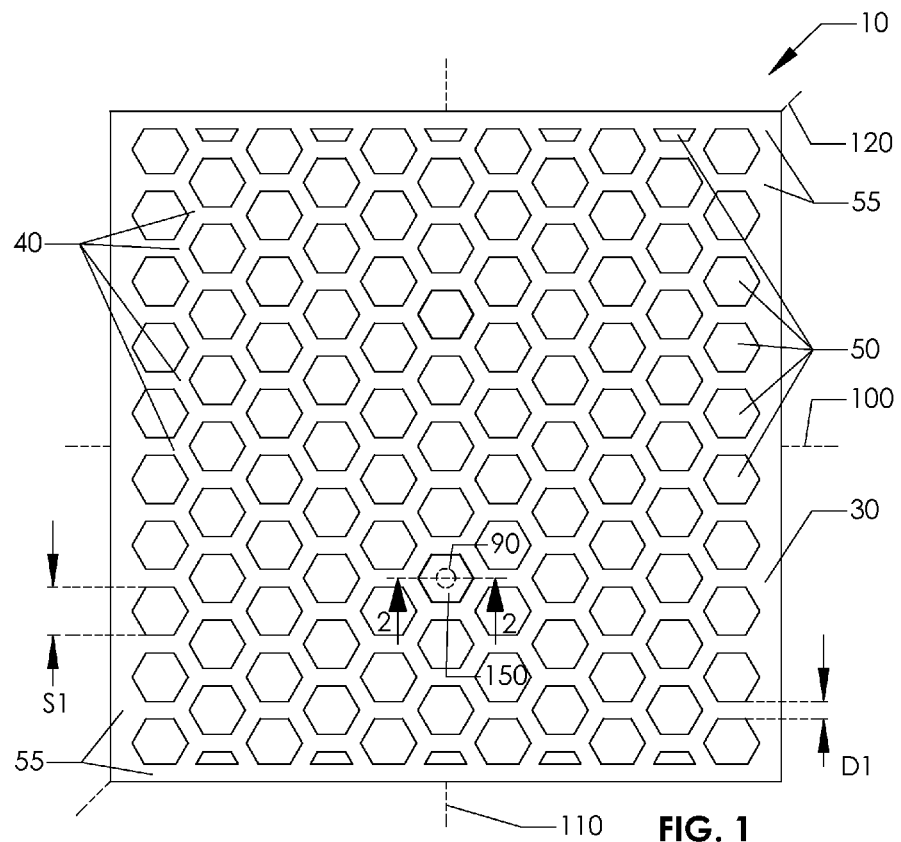
FIG. 1 is a schematic of a tear-resistant dental dam in accordance with an exemplary embodiment.
Figure 2:
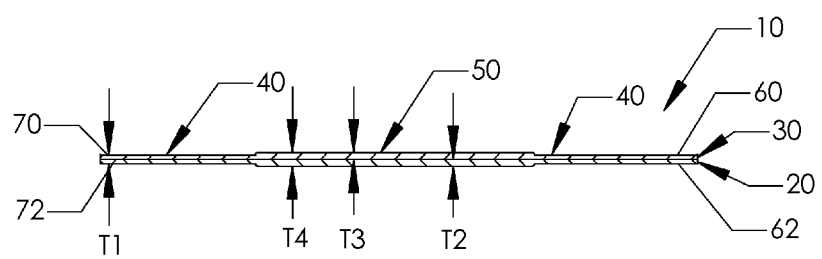
FIG. 2 is a cross-sectional schematic of a portion of the tear-resistant dental dam of FIG. 1.

Referring to FIGS. 1 and 2, a tear-resistant dental dam 10 in accordance with an exemplary embodiment is illustrated. The tear-resistant dental dam 10 includes a first elastomeric sheet 20 and a second elastomeric sheet 30 disposed on the first elastomeric sheet 20. The first and second elastomeric sheets 20, 30 have a grid pattern of weld joint regions 40 configured to couple together the first and second elastomeric sheets 20, 30. In the grid pattern of weld joint regions 40, a portion of the first elastomeric sheet 20 is welded to the second elastomeric sheet 30. The grid pattern of weld joint regions 40 define a plurality of unwelded regions 50 of the first and second elastomeric sheets 20, 30. The first and second elastomeric sheets 20, 30 further include a peripheral weld joint region 55 that extends around an outer periphery of the first elastomeric sheet 20 and an outer periphery of the second elastomeric sheet 30 such that the first and second elastomeric sheets 20, 30 are further coupled together at the peripheral weld joint region 55. An advantage of the tear-resistant dental dam 10 is that the dental dam 10 utilizes the grid pattern of weld joint regions 40 and the plurality of unwelded regions 50 of the first and second elastomeric sheets 20, 30 to reduce tear propagation in the dental dam 10 as will be explained in greater detail below.

In one exemplary embodiment, the first and second elastomeric sheets 20, 30 are constructed of a thermoplastic elastomer. For example, the first and second elastomeric sheets 20, 30 could be constructed of polyisoprene. Further, in one exemplary embodiment, the first and second elastomeric sheets 20, 30 are constructed of a non-latex elastomer. In an alternative embodiment, other elastomeric materials, such as latex for example, could be utilized to construct the first and second elastomeric sheets 20, 30. In the illustrated embodiment, the first and second elastomeric sheets 20, 30 have a similar peripheral size. In an alternative embodiment, the first and second elastomeric sheets 20, 30 could have a different peripheral size from one another. In one exemplary embodiment, each of the first and second elastomeric sheets 20, 30 have a thickness in a range of 0.002-0.04 inches. Also, in an exemplary embodiment, the first and second elastomeric sheets 20, 30 have dimensions of 6 inches×6 inches. However, in alternative embodiments, the first and second elastomeric sheets 20, 30 could have different dimensions (e.g., 5 inches×5 inches) depending on the desired dental procedure or other desired use. As shown, the elastomeric sheet 20 includes a first side 60 and a second side 62 disposed opposite to the first side 60. Further, the elastomeric sheet 30 includes a first side 70 and a second side 72 disposed opposite to the first side 70.

In the grid pattern of weld joint regions 40, weld joints are formed in at least the first side 60 of the first elastomeric sheet 20 and the second side 72 of the second elastomeric sheet 30. Also, in the plurality of unwelded regions 50, the first side 60 of the first elastomeric sheet 20 and the second side 72 of the second elastomeric sheet 30 are disposed adjacent to each other but are not welded together.

Referring to FIG. 2, in one exemplary embodiment, in the grid pattern of weld joint regions 40, a thickness T1 of the first and second elastomeric sheets 20, 30 is greater than a thickness T2 of the first elastomeric sheet 20 in an unwelded region of the plurality of unwelded regions 50. Further, the thickness T1 of the first and second elastomeric sheets 20, 30 is greater than a thickness T3 of the second elastomeric sheet 30 in an unwelded region of the plurality of unwelded regions 50. Thus, if a tear occurs in the second elastomeric sheet 30 in the unwelded region 50, an adjacent weld joint region 40 having a greater thickness than the second elastomeric sheet 30 will tend to stop the tear from propagating across the adjacent weld joint region 40. In one exemplary embodiment, a thickness T4 of the first and second elastomeric sheets 20, 30 in the plurality of unwelded regions 50 is greater than a thickness T1 of the first and second elastomeric sheets 20, 30 in the grid pattern of weld joint regions 40. Of course, in an alternative embodiment, the thickness T4 could be substantially equal to the thickness T1.

Referring to FIG. 1, as discussed above, the grid pattern of weld joint regions 40 define a plurality of unwelded regions 50. In the exemplary embodiment, the plurality of unwelded regions 50 comprise a plurality of polygon-shaped unwelded regions. An advantage of each polygon-shaped unwelded region 50 is that this configuration effectively disperses adjacent stresses to the weld joint regions 40 disposed adjacent to the polygon-shaped unwelded region 50 to reduce and/or prevent tear propagation. Of course, in an alternative embodiment, the plurality of unwelded regions 50 could have other enclosed shapes or other substantially enclosed shapes.

In the exemplary embodiment, a size S1 across at least one unwelded region of the plurality of polygon-shaped unwelded regions 50 is in a range of 2-20 millimeters. An advantage of an unwelded region 50 having a size S1 in a range of 2-20 millimeters is that the respective unwelded region 50 can effectively surround a tooth extending through an aperture 90 punched in the dental dam 10. In an alternative embodiment, the plurality of unwelded regions 50 could have other sizes depending on the desired application of the dental dam 10. In another alternative embodiment, the plurality of unwelded regions 50 can have an alternate shape or size or both, or have a plurality of alternating shapes and/or sizes to accommodate different applications in dental procedures.

Also, in the exemplary embodiment, the plurality of polygon-shaped unwelded regions 50 are positioned such that at least one side of each polygon-shaped unwelded region 50 is disposed a distance D1 from a proximate side of another polygon-shaped unwelded region 50. In one exemplary embodiment, the distance D1 is in a range of 2-6 millimeters. An advantage of the distance D1 being in a range of 2-6 millimeters is that a portion of a weld joint region 40 disposed proximate to an aperture 90 punched through the dental dam 10 can be effectively disposed between adjacent teeth where the adjacent teeth are in close proximity to one another. Of course, in an alternative embodiment, the distance D1 could be less than 2 millimeters or greater than 6 millimeters.

A further advantage of the configuration of the grid pattern of weld joint regions 40 is that tear propagation is further inhibited because the plurality of unwelded polygon-shaped regions 50 are positioned such that a tear cannot propagate in a straight line across a central portion of the dental dam 10 without contacting at least one unwelded region 50 and at least one weld joint region 40. For example, a plane 100 bisecting the first and second elastomeric sheets 20, 30 and extending through an outer side of the first elastomeric sheet 20 to an outer side of the second elastomeric sheet 30 will contact at least one unwelded region of the plurality of unwelded regions 50 and at least a portion of the grid pattern of weld joint regions 40. Similarly, a plane 110 bisecting the first and second elastomeric sheets 20, 30 and extending through an outer side of the first elastomeric sheet 20 to an outer side of the second elastomeric sheet 30 will contact at least one unwelded region of the plurality of unwelded regions 50 and at least a portion of the grid pattern of weld joint regions 40. Still further, a plane 120 bisecting the first and second elastomeric sheets 20, 30 and extending through an outer side of the first elastomeric sheet 20 to an outer side of the second elastomeric sheet 30 will contact at least one unwelded region of the plurality of unwelded regions 50 and at least a portion of the grid pattern of weld joint regions 40.

Figure 3:
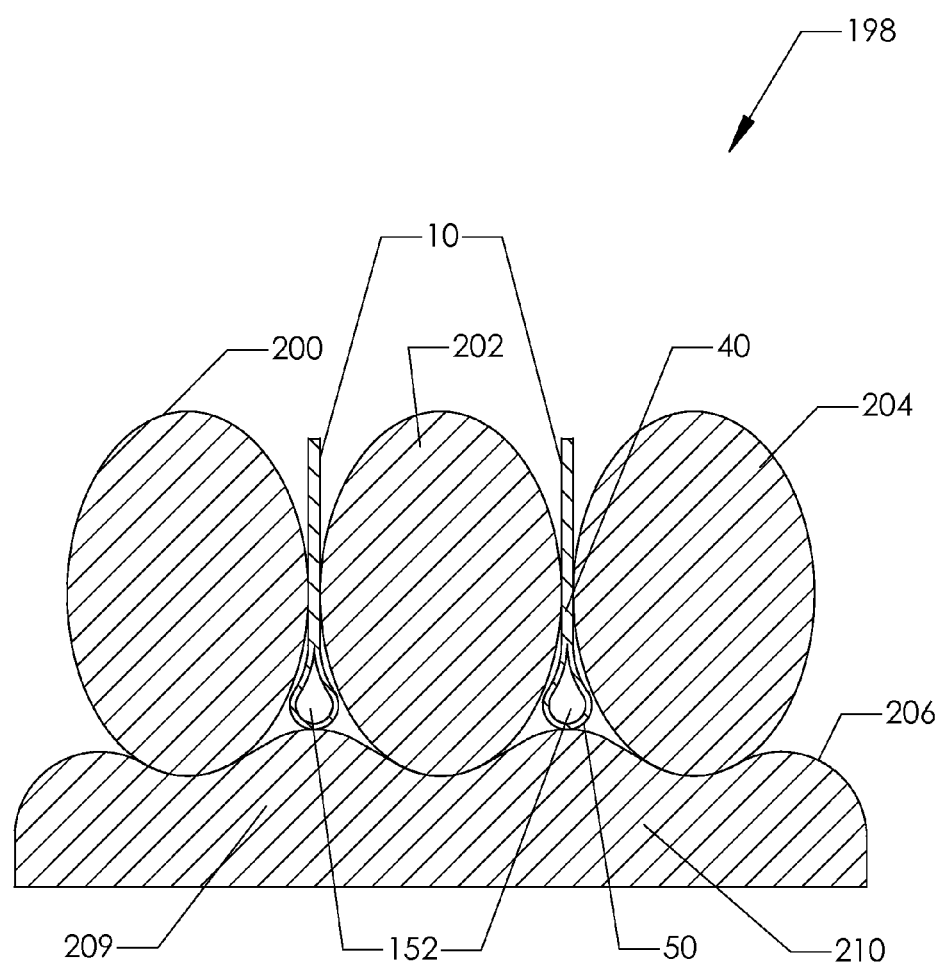
FIG. 3 is a cross-sectional schematic of a portion of a human mouth and a portion of the dental dam of FIG. 1.

Referring to FIGS. 1 and 3, a cross-sectional schematic of a portion of a human mouth 198 and a portion of the dental dam 10 are illustrated. The human mouth 198 includes teeth 200, 202, 204 and a gingival tissue 206. The gingival tissue 206 surrounds and supports a lower portion of the teeth 200, 202, 204. To isolate the tooth 202 during a dental procedure, a dentist may punch the aperture 90 through the first and second elastomeric sheets 20, 30 of the dental dam 10 utilizing a punching device. The aperture 90 is sized to receive the tooth 202 therethrough. Thereafter, the dentist can position the dental dam 10 in the human mouth 198 such that the tooth 202 extends through the aperture 90 in the dental dam 10. An unwelded region 50 of the dental dam 10 is disposed around the tooth 200, and as shown is disposed in a lower gap 209 between the teeth 202, 200 and in a lower gap 210 between the teeth 202, 204. A small air gap 152 is formed between the first and second elastomeric sheets 20, 30 in the unwelded region 50 of the dental dam 10 proximate to the aperture 90. An advantage of the small air gap 152 is that the unwelded region 50 can be effectively wedged within the lower gaps 209, 210 while the welded region 40 is compressed between the adjacent teeth 200 and 204 to allow the dental dam 10 to be affixed to the tooth 202 without utilizing a dental dam clamp.

Figure 4:
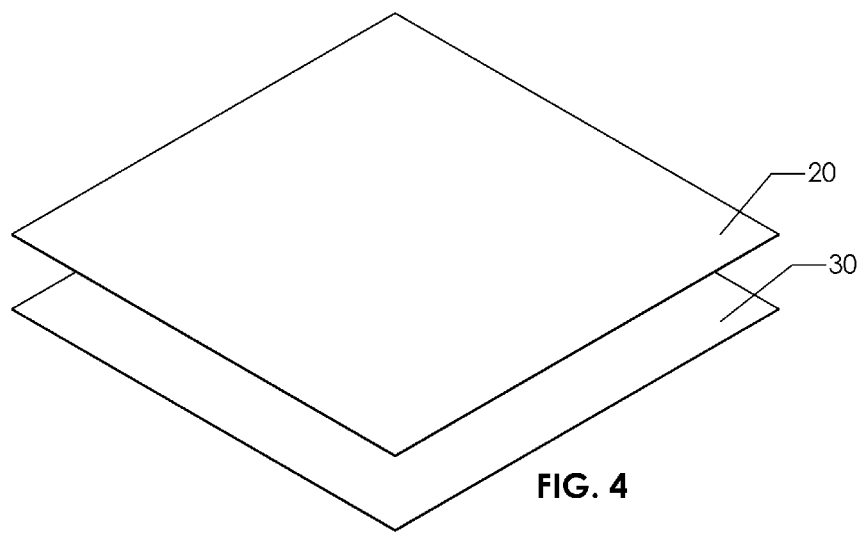
FIG. 4 is a schematic of first and second elastomeric sheets utilized to construct the tear-resistant dental dam of FIG. 1.

Referring to FIG. 4, in one exemplary manufacturing process, prior to the elastomeric sheets 20, 30 being welded together to form the dental dam 10, the elastomeric sheets 20, 30 are distinct sheets. In one exemplary embodiment, the elastomeric sheets 20, 30 have a substantially equal peripheral size. Of course, in an alternative embodiment, the elastomeric sheets 20, 30 could have a different peripheral sizes from one another.

Figures 5, 6, 7:
FIG. 5 is a block diagram of a hot plate welding device that can be utilized to construct the tear-resistant dental dam of FIG. 1.
FIG. 6 is a block diagram of an ultrasonic welding device that can be utilized to construct the tear-resistant dental dam of FIG. 1.
FIG. 7 is a block diagram of a radio-frequency welding device that can be utilized to construct the tear-resistant dental dam of FIG. 1.

Referring to FIGS. 1 and 5, a hot plate welding device 230 is illustrated. In one exemplary manufacturing method, the hot plate welding device 230 can utilize one or more heated members to contact at least one of the elastomeric sheets 20, 30 shown in FIG. 4 that are adjacently disposed to one another to form the grid pattern of weld joint regions 40 and the peripheral weld joint region 55 in the elastomeric sheets 20, 30.

Referring to FIGS. 1 and 6, an ultrasonic welding device 240 is illustrated. In another exemplary manufacturing method, the ultrasonic welding device 240 can contact at least one of elastomeric sheets 20, 30 shown in FIG. 4 adjacently disposed to one another to form the grid pattern of weld joint regions 40 and the peripheral weld joint region 55 in the elastomeric sheets 20, 30.

Referring to FIGS. 1 and 7, a radio-frequency welding device 250 is illustrated. In another exemplary manufacturing method, the radio-frequency welding device 250 can contact at least one of elastomeric sheets 20, 30 shown in FIG. 4 adjacently disposed to one another to form the grid pattern of weld joint regions 40 and the peripheral weld joint region 55 on the elastomeric sheets 20, 30.

Second Dental Dam Embodiment

Referring to FIGS. 8 and 9, a tear-resistant dental dam 310 in accordance with another exemplary embodiment is illustrated. The tear-resistant dental dam 310 includes a first elastomeric sheet 320 and a second elastomeric sheet 330 disposed on the first elastomeric sheet 320. The first and second elastomeric sheets 320, 330 have a grid pattern of weld joint regions 340 configured to couple together the first and second elastomeric sheets 320, 330. In the grid pattern of weld joint regions 340, a portion of the first elastomeric sheet 320 is welded to the second elastomeric sheet 330. The grid pattern of weld joint regions 340 define a plurality of unwelded regions 350 of the first and second elastomeric sheets 320, 330. The first and second elastomeric sheets 320, 330 further include a peripheral weld joint region 355 that extends around an outer periphery of the first elastomeric sheet 320 and an outer periphery of the second elastomeric sheet 330 such that the first and second elastomeric sheets 320, 330 are further coupled together at the peripheral weld joint region 355. An advantage of the tear-resistant dental dam 310 is that the dental dam 310 utilizes the grid pattern of weld joint regions 340 and the plurality of unwelded regions 350 of the first and second elastomeric sheets 320, 330 to reduce tear propagation in the dental dam 310 as will be explained in greater detail below.

In one exemplary embodiment, the first and second elastomeric sheets 320, 330 are constructed of a thermoplastic elastomer. For example, the first and second elastomeric sheets 320, 330 could be constructed of polyisoprene. Further, in one exemplary embodiment, the first and second elastomeric sheets 320, 330 are constructed of a non-latex elastomer. In an alternative embodiment, other elastomeric materials, such as latex for example, could be utilized to construct the first and second elastomeric sheets 320, 330. In the illustrated embodiment, the first and second elastomeric sheets 320, 330 have a similar peripheral size. In an alternative embodiment, the first and second elastomeric sheets 320, 330 could have a different peripheral size from one another. In one exemplary embodiment, each of the first and second elastomeric sheets 320, 330 have a thickness in a range of 0.002-0.04 inches. As shown, the elastomeric sheet 320 includes a first side 360 and a second side 362 disposed opposite to the first side 360. Further, the elastomeric sheet 330 includes a first side 370 and a second side 372 disposed opposite to the first side 370.

In the grid pattern of weld joint regions 340, weld joints are formed in the first side 360 of the first elastomeric sheet 320 and the second side 372 of the second elastomeric sheet 330. Also, in the plurality of unwelded regions 350, the first side 360 of the first elastomeric sheet 320 and the second side 372 of the second elastomeric sheet 330 are disposed adjacent to each other but are not welded together.

Referring to FIG. 9, in one exemplary embodiment, in the grid pattern of weld joint regions 340, a thickness T5 of the first and second elastomeric sheets 320, 330 is greater than a thickness T6 of the first elastomeric sheet 320 in an unwelded region of the plurality of unwelded regions 350. Further, the thickness T5 of the first and second elastomeric sheets 320, 330 is greater than a thickness T7 of the second elastomeric sheet 330 in an unwelded region of the plurality of unwelded regions 350. Thus, if a tear occurs in the second elastomeric sheet 330 in the unwelded region 350, an adjacent weld joint region 340 having a greater thickness than the second elastomeric sheet 330 will tend to stop the tear from propagating across the adjacent weld joint region 340. In one exemplary embodiment, a thickness T8 of the first and second elastomeric sheets 320, 330 in the plurality of unwelded regions 350 is greater than a thickness T5 of the first and second elastomeric sheets 320, 330 in the grid pattern of weld joint regions 340. Of course, in an alternative embodiment, the thickness T8 could be substantially equal to the thickness T5.

Referring to FIG. 8, as discussed above, the grid pattern of weld joint regions 340 define a plurality of unwelded regions 350. In the exemplary embodiment, the plurality of unwelded regions 350 comprise a plurality of rectangular-shaped unwelded regions. An advantage of each rectangular-shaped unwelded region 350 is that this configuration disperses adjacent stresses to the weld joint regions 340 disposed adjacent to the rectangular-shaped unwelded region 350 to reduce and/or prevent tear propagation. Of course, in an alternative embodiment, the plurality of unwelded regions 350 could have other enclosed shapes or other substantially enclosed shapes, or alternating shapes or sizes.

In the exemplary embodiment, a size S2 across at least one unwelded region of the plurality of rectangular-shaped unwelded regions 350 is in a range of 2-20 millimeters. An advantage of an unwelded region 350 having a size S2 in a range of 2-20 millimeters is that the respective unwelded region 350 can effectively surround a tooth extending through an aperture 390 punched in the dental dam 310. In an alternative embodiment, the plurality of unwelded regions 350 could have other sizes, or alternating shapes or sizes, depending on the desired application of the dental dam 310.

Also, in the exemplary embodiment, the plurality of rectangular-shaped unwelded regions 350 are positioned such that at least one side of each rectangular-shaped unwelded region 350 is disposed a distance D2 from a proximate side of another rectangular-shaped unwelded region 350. In one exemplary embodiment, the distance D2 is in a range of 2-6 millimeters. An advantage of the distance D2 being in a range of 2-6 millimeters is that a portion of a weld joint region 340 disposed proximate to an aperture 390 punched through the dental dam 310 can be effectively disposed between adjacent teeth where the adjacent teeth are in close proximity to one another. Of course, in an alternative embodiment, the distance D2 could be less than 2 millimeters or greater than 6 millimeters.

A further advantage of the configuration of the grid pattern of weld joint regions 340 is that tear propagation is further inhibited because the plurality of unwelded rectangular-shaped regions 350 are positioned such that a tear cannot easily propagate in a straight line across a central portion of the dental dam 310 without contacting at least one unwelded region 350 and at least one weld joint region 340. For example, a plane 400 bisecting the first and second elastomeric sheets 320, 330 and extending through an outer side of the first elastomeric sheet 320 to an outer side of the second elastomeric sheet 330 will contact at least one unwelded region of the plurality of unwelded regions 350 and at least a portion of the grid pattern of weld joint regions 340. Similarly, a plane 410 bisecting the first and second elastomeric sheets 320, 330 and extending through an outer side of the first elastomeric sheet 320 to an outer side of the second elastomeric sheet 330 will contact at least one unwelded region of the plurality of unwelded regions 350 and at least a portion of the grid pattern of weld joint regions 340. Still further, a plane 420 bisecting the first and second elastomeric sheets 320, 330 and extending through an outer side of the first elastomeric sheet 320 to an outer side of the second elastomeric sheet 330 will contact at least one unwelded region of the plurality of unwelded regions 350 and at least a portion of the grid pattern of weld joint regions 340.

Referring to FIGS. 5-7 and 8, the dental dam 310 can be constructed utilizing at least one of the hot plate welding device 230, the ultrasonic welding device 240, and the radio-frequency welding device 250.

Third Dental Dam Embodiment

Figure 10:
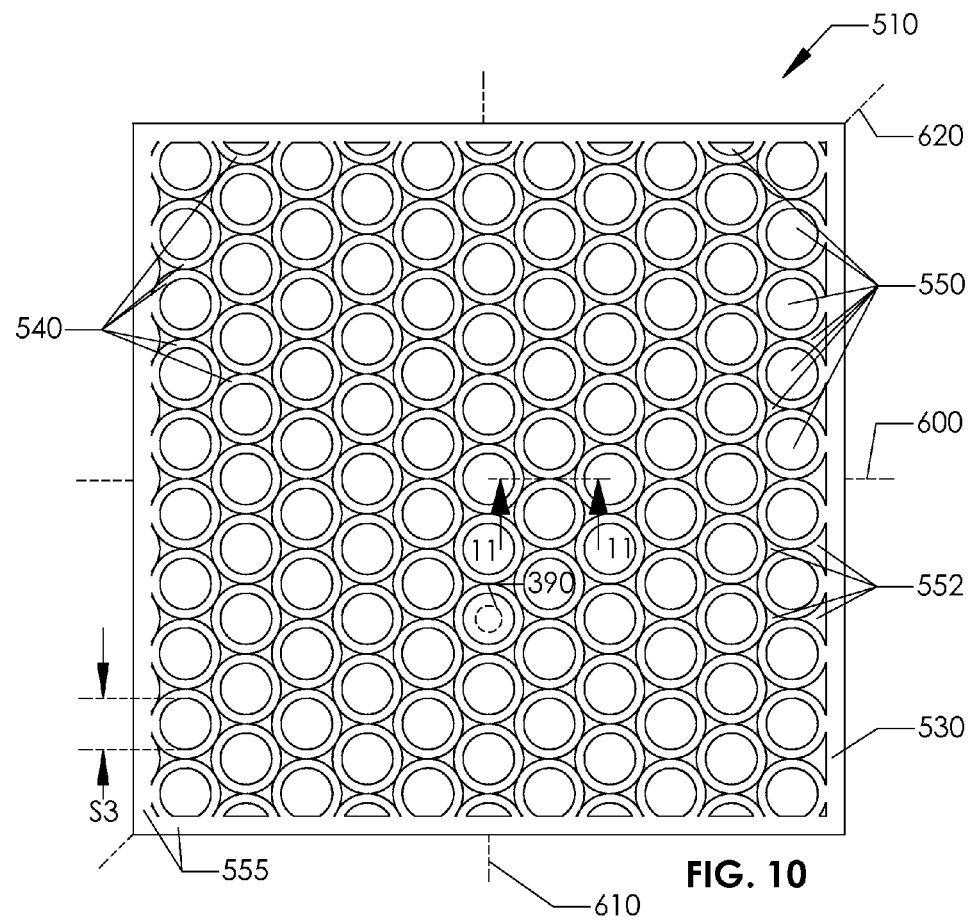
FIG. 10 is a schematic of a tear-resistant dental dam in accordance with another exemplary embodiment.
Figure 11:
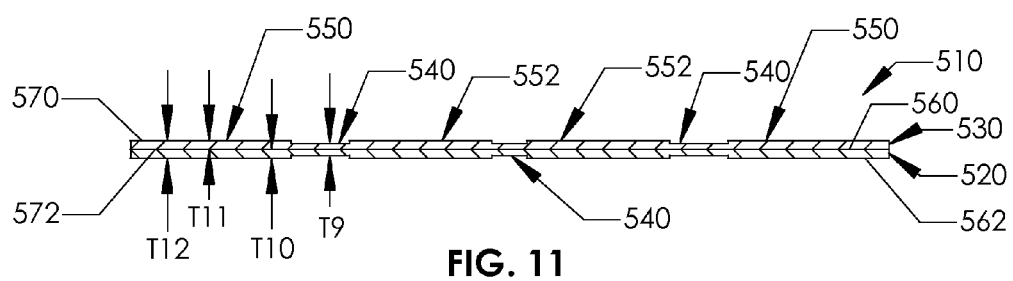
FIG. 11 is a cross-sectional schematic of a portion of the tear-resistant dental dam of FIG. 10.

Referring to FIGS. 10 and 11, a tear-resistant dental dam 510 in accordance with another exemplary embodiment is illustrated. The tear-resistant dental dam 510 includes a first elastomeric sheet 520 and a second elastomeric sheet 530 disposed on the first elastomeric sheet 520. The first and second elastomeric sheets 520, 530 have a grid pattern of weld joint regions 540 configured to couple together the first and second elastomeric sheets 520, 530. In the grid pattern of weld joint regions 540, a portion of the first elastomeric sheet 520 is welded to the second elastomeric sheet 530. The grid pattern of weld joint regions 540 define a plurality of unwelded regions 550 of the first and second elastomeric sheets 520, 530. The first and second elastomeric sheets 520, 530 further include a peripheral weld joint region 555 that extends around an outer periphery of the first elastomeric sheet 520 and an outer periphery of the second elastomeric sheet 530 such that the first and second elastomeric sheets 520, 530 are further coupled together at the peripheral weld joint region 555. An advantage of the tear-resistant dental dam 510 is that the dental dam 510 utilizes the grid pattern of weld joint regions 540 and the plurality of unwelded regions 550 of the first and second elastomeric sheets 520, 530 to reduce tear propagation in the dental dam 310 as will be explained in greater detail below.

In one exemplary embodiment, the first and second elastomeric sheets 520, 530 are constructed of a thermoplastic elastomer. For example, the first and second elastomeric sheets 520, 530 could be constructed of polyisoprene. Further, in one exemplary embodiment, the first and second elastomeric sheets 520, 530 are constructed of a non-latex elastomer. In an alternative embodiment, other elastomeric materials, such as latex for example, could be utilized to construct the first and second elastomeric sheets 520, 530. In the illustrated embodiment, the first and second elastomeric sheets 520, 530 have a similar peripheral size. In an alternative embodiment, the first and second elastomeric sheets 520, 530 could have a different peripheral size from one another. In one exemplary embodiment, each of the first and second elastomeric sheets 520, 530 have a thickness in a range of 0.002-0.04 inches. As shown, the elastomeric sheet 520 includes a first side 560 and a second side 562 disposed opposite to the first side 560. Further, the elastomeric sheet 530 includes a first side 570 and a second side 572 disposed opposite to the first side 570.

In the grid pattern of weld joint regions 540, weld joints are formed in at least the first side 560 of the first elastomeric sheet 520 and the second side 572 of the second elastomeric sheet 530. Also, in the plurality of unwelded regions 550, the first side 560 of the first elastomeric sheet 520 and the second side 572 of the second elastomeric sheet 530 are disposed adjacent to each other but are not welded together.

Referring to FIG. 11, in one exemplary embodiment, in the grid pattern of weld joint regions 540, a thickness T9 of the first and second elastomeric sheets 520, 530 is greater than a thickness T10 of the first elastomeric sheet 520 in an unwelded region of the plurality of unwelded regions 550. Further, the thickness T9 of the first and second elastomeric sheets 520, 530 is greater than a thickness T11 of the second elastomeric sheet 530 in an unwelded region of the plurality of unwelded regions 550. Thus, if a tear occurs in the second elastomeric sheet 530 in the unwelded region 550, an adjacent weld joint region 540 having a greater thickness than the second elastomeric sheet 530 will tend to stop the tear from propagating across the adjacent weld joint region 540. In one exemplary embodiment, a thickness T12 of the first and second elastomeric sheets 520, 530 in the plurality of unwelded regions 550 is greater than a thickness T9 of the first and second elastomeric sheets 520, 530 in the grid pattern of weld joint regions 540. Of course, in an alternative embodiment, the thickness T12 could be substantially equal to the thickness T9.

Referring to FIG. 10, in the exemplary embodiment, the grid pattern of weld joint regions 540 comprise a plurality of ring-shaped weld joint regions that extend from one another and define a plurality of unwelded regions 550 and a plurality of unwelded regions 552. In the exemplary embodiment, the plurality of unwelded regions 550 comprise a plurality of circular-shaped unwelded regions, and the plurality of unwelded regions 552 comprise a plurality of triangular-shaped unwelded regions. An advantage of each circular-shaped unwelded region 550 is that this configuration disperses adjacent stresses to the weld joint regions 540 disposed adjacent to the circular-shaped unwelded region 550 to reduce and/or prevent tear propagation. Of course, in an alternative embodiment, the plurality of unwelded regions 550 could have other enclosed shapes or other substantially enclosed shapes, or alternative shapes and/or sizes. Further, the plurality of unwelded regions 552 could have other enclosed shapes or other substantially enclosed shapes. In another alternative embodiment, the regions 552 could be welded regions.

In the exemplary embodiment, a size S3 across at least one unwelded region of the plurality of circular-shaped unwelded regions 550 is in a range of 2-20 millimeters. An advantage of an unwelded region 550 having a size S3 in a range of 2-20 millimeters is that the respective unwelded region 550 can effectively surround a tooth extending through an aperture 590 punched in the dental dam 510. In an alternative embodiment, the plurality of unwelded regions 550 could have other sizes depending on the desired application of the dental dam 510. In another alternative embodiment, the unwelded regions 550 could have alternating shapes and/or sizes.

A further advantage of the configuration of the grid pattern of weld joint regions 540 is that tear propagation is further inhibited because the plurality of unwelded circular-shaped regions 550 are positioned such that a tear cannot propagate in a straight line across a central portion of the dental dam 510 without contacting at least one unwelded region 550 and at least one weld joint region 540. For example, a plane 600 bisecting the first and second elastomeric sheets 520, 530 and extending through an outer side of the first elastomeric sheet 520 to an outer side of the second elastomeric sheet 530 will contact at least one unwelded region of the plurality of unwelded regions 550 and at least a portion of the grid pattern of weld joint regions 540. Similarly, a plane 610 bisecting the first and second elastomeric sheets 520, 530 and extending through an outer side of the first elastomeric sheet 520 to an outer side of the second elastomeric sheet 530 will contact at least one unwelded region of the plurality of unwelded regions 550 and at least a portion of the grid pattern of weld joint regions 540. Still further, a plane 620 bisecting the first and second elastomeric sheets 520, 530 and extending through an outer side of the first elastomeric sheet 520 to an outer side of the second elastomeric sheet 530 will contact at least one unwelded region of the plurality of unwelded regions 550 and at least a portion of the grid pattern of weld joint regions 540.

Referring to FIGS. 5-7 and 10, the dental dam 510 can be constructed utilizing at least one of the hot plate welding device 230, the ultrasonic welding device 240, and the radio-frequency welding device 250.

Fourth Dental Dam Embodiment

Figure 14:
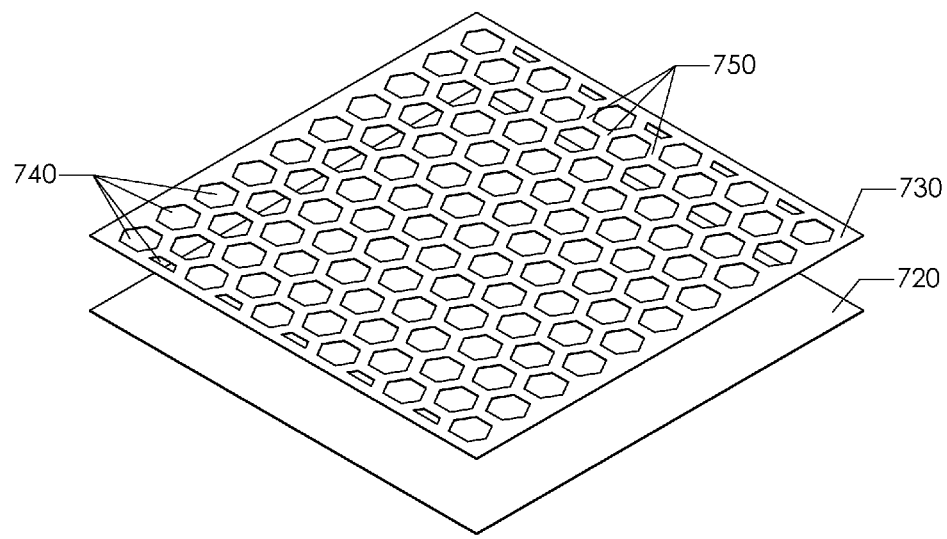
FIG. 14 is a schematic of first and second elastomeric sheets utilized to construct the tear-resistant dental dam of FIG. 13.

Referring to FIGS. 12-14, a tear-resistant dental dam 710 in accordance with another exemplary embodiment is illustrated. The tear-resistant dental dam 710 includes a first elastomeric sheet 720 and a second elastomeric sheet 730 disposed on the first elastomeric sheet 720. The second elastomeric sheet 730 has a plurality of apertures 740 extending therethrough that define a grid pattern of elastomeric material 750 of the second elastomeric sheet 730. The grid pattern of elastomeric material 750 is coupled to the first elastomeric sheet 720 in a grid pattern of weld joint regions 760. An advantage of the tear-resistant dental dam 710 is that the dental dam 710 utilizes the grid pattern of elastomeric material 750 to reduce tear propagation in the dental dam 710 as will be explained in greater detail below.

In one exemplary embodiment, the grid pattern of elastomeric material 750 is welded to the first elastomeric sheet 720 utilizing a solvent that forms weld joints in the first and second elastomeric sheets 720, 730. Of course, in an alternative embodiment, other types of welding methodologies disclosed herein.

In the exemplary embodiment, the first and second elastomeric sheets 720, 730 are constructed of a thermoplastic elastomer. For example, the first and second elastomeric sheets 720, 730 could be constructed of polyisoprene. Further, in one exemplary embodiment, the first and second elastomeric sheets 720, 730 are constructed of a non-latex elastomer. In an alternative embodiment, other elastomeric materials, such as latex for example, could be utilized to construct the first and second elastomeric sheets 720, 730. In the illustrated embodiment, the first and second elastomeric sheets 720, 730 have a similar peripheral size. In an alternative embodiment, the first and second elastomeric sheets 720, 730 could have a different peripheral size from one another. In one exemplary embodiment, each of the first and second elastomeric sheets 720, 730 have a thickness in a range of 0.002-0.04 inches. As shown, the elastomeric sheet 720 includes a first side 761 and a second side 762 disposed opposite to the first side 761. Further, the elastomeric sheet 730 includes a first side 770 and a second side 772 disposed opposite to the first side 770. Weld joints are formed in the first side 761 of the first elastomeric sheet 720 and the second side 772 of the second elastomeric sheet 730 in the grid pattern of weld joint regions 760.

Referring to FIG. 13, in one exemplary embodiment, in the grid pattern of weld joint regions 760, a thickness T13 of the first and second elastomeric sheets 720, 730 is greater than a thickness T14 of the first elastomeric sheet 720. Thus, if a tear occurs in the first elastomeric sheet 720 at an aperture 740, the adjacent weld joint region 760 having a greater thickness than the first elastomeric sheet 720 will tend to stop the tear from propagating across the adjacent weld joint region 760. In one exemplary embodiment, a thickness T14 of the first elastomeric sheet 720 is greater than a thickness T15 of the second elastomeric sheet 730. Of course, in an alternative embodiment, the thickness T14 could be substantially equal to the thickness T15.

Referring to FIGS. 12 and 14, in one exemplary embodiment, the plurality of apertures 740 extending through the second elastomeric sheet 730 are a plurality of polygon-shaped apertures. In particular, the plurality of apertures 740 are a plurality of hexagonal-shaped apertures. An advantage of each hexagonal-shaped aperture 740 is that this configuration disperses adjacent stresses to the weld joint regions 760 having a corresponding hexagonal-shaped region disposed adjacent to the hexagonal-shaped aperture 740 to reduce and/or prevent tear propagation. Of course, in an alternative embodiment, the plurality of apertures 740 could have other shapes. In another alternative embodiment, the apertures 740 could have alternating shapes and/or sizes.

In the exemplary embodiment, a size S4 across at least one aperture 740 is in a range of 2-20 millimeters. An advantage of an aperture 740 having a size S4 in a range of 2-20 millimeters is that the underlying layer 720 proximate to the aperture 740 can effectively surround a tooth extending through an aperture 790 punched in the dental dam 710. In an alternative embodiment, the aperture 740 could have other sizes depending on the desired application of the dental dam. In another alternative embodiment, the apertures 740 could have alternating shapes and/or sizes.

A further advantage of the configuration of the weld joint regions 760 is that tear propagation is further inhibited because the weld joint regions 760 are positioned such that a tear cannot propagate in a straight line across a central portion of the dental dam 710 without contacting at least one weld joint region 760. For example, a plane 800 bisecting the first and second elastomeric sheets 720, 730 and extending through an outer side of the first elastomeric sheet 720 to an outer side of the second elastomeric sheet 730 will contact at least one weld joint region 760. Similarly, a plane 810 bisecting the first and second elastomeric sheets 720, 730 and extending through an outer side of the first elastomeric sheet 720 to an outer side of the second elastomeric sheet 730 will contact at least one weld joint region 760. Still further, a plane 820 bisecting the first and second elastomeric sheets 720, 730 and extending through an outer side of the first elastomeric sheet 720 to an outer side of the second elastomeric sheet 730 will contact at least one weld joint region 760.

Referring to FIG. 14, in an exemplary manufacturing process, prior to the first and second elastomeric sheets 720, 730 being welded together to form the dental dam 710, the elastomeric sheets 720, 730 are distinct sheets. In one exemplary embodiment, the first elastomeric sheet 730 has the plurality of apertures 740 pre-cut therethrough. In one exemplary embodiment, the elastomeric sheets 720, 730 have a substantially equal peripheral size to one another. Of course, in an alternative embodiment, the elastomeric sheets 720, 730 could have a different peripheral sizes from one another.

Figure 15:
FIG. 15 is a block diagram of a solvent welding device that can be utilized to construct the tear-resistant dental dam of FIG. 12.

Referring to FIGS. 13-15, a solvent welding device 850 is illustrated. In one exemplary manufacturing method, the solvent welding device 850 can utilize a solvent that contacts the elastomeric sheets 720, 730 that are adjacently disposed to one another to weld the first and second elastomeric sheet 720, 730 to one another.

Fifth Dental Dam Embodiment

Figure 16:
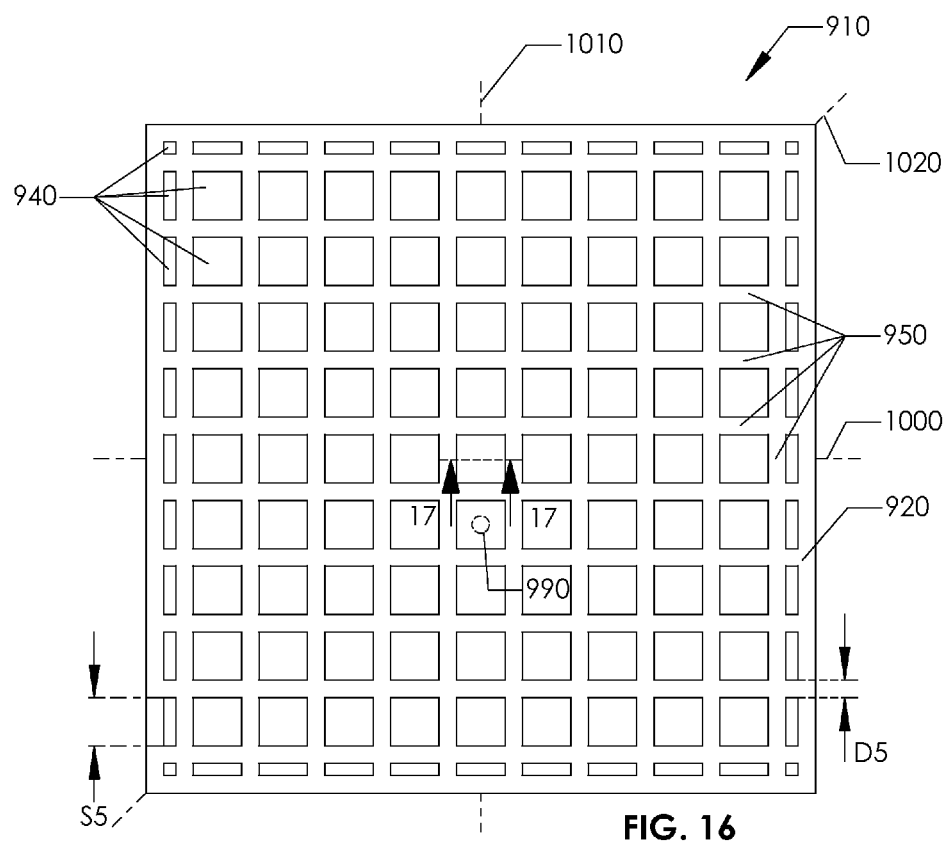
FIG. 16 is a schematic of a tear-resistant dental dam in accordance with another exemplary embodiment.
Figure 17:
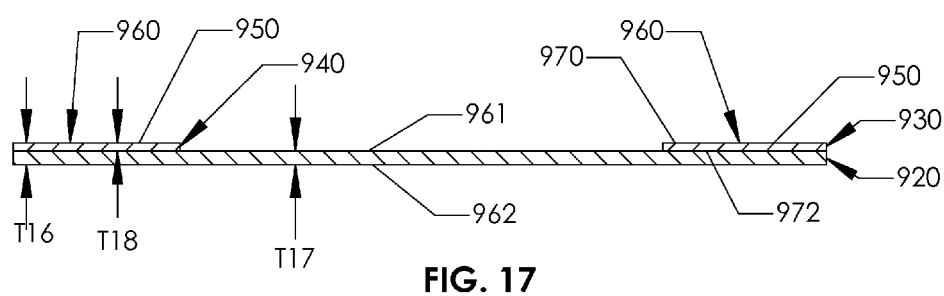
FIG. 17 is a cross-sectional schematic of a portion of the tear-resistant dental dam of FIG. 16.
Figure 18:
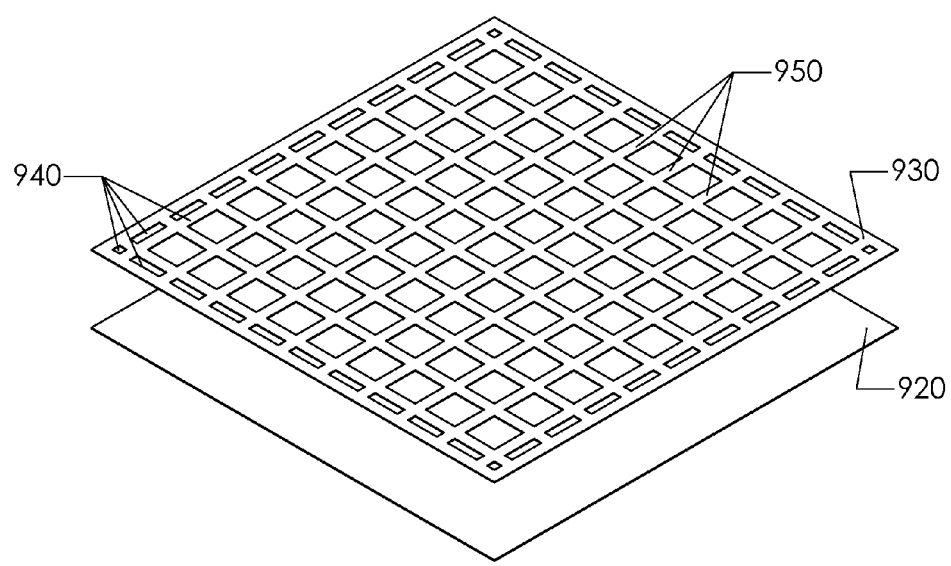
FIG. 18 is a schematic of first and second elastomeric sheets utilized to construct the tear-resistant dental dam of FIG. 16.

Referring to FIGS. 16-18, a tear-resistant dental dam 910 in accordance with another exemplary embodiment is illustrated. The tear-resistant dental dam 910 includes a first elastomeric sheet 920 and a second elastomeric sheet 930 disposed on the first elastomeric sheet 920. The second elastomeric sheet 930 has a plurality of apertures 940 extending therethrough that define a grid pattern of elastomeric material 950 of the second elastomeric sheet 930. The grid pattern of elastomeric material 950 is coupled to the first elastomeric sheet 920 in a grid pattern of weld joint regions 960. An advantage of the tear-resistant dental dam 910 is that the dental dam 910 utilizes the grid pattern of elastomeric material 950 to reduce tear propagation in the dental dam 910 as will be explained in greater detail below.

In one exemplary embodiment, the grid pattern of elastomeric material 950 is welded to the first elastomeric sheet 920 utilizing a solvent that forms weld joints in the first and second elastomeric sheets 920, 930. Of course, in an alternative embodiment, other types of welding methodologies disclosed herein.

In the exemplary embodiment, the first and second elastomeric sheets 920, 930 are constructed of a thermoplastic elastomer. For example, the first and second elastomeric sheets 920, 930 could be constructed of polyisoprene. Further, in one exemplary embodiment, the first and second elastomeric sheets 920, 930 are constructed of a non-latex elastomer. In an alternative embodiment, other elastomeric materials, such as latex for example, could be utilized to construct the first and second elastomeric sheets 920, 930. In the illustrated embodiment, the first and second elastomeric sheets 920, 930 have a similar peripheral size. In an alternative embodiment, the first and second elastomeric sheets 920, 930 could have a different peripheral size from one another. In one exemplary embodiment, each of the first and second elastomeric sheets 920, 930 have a thickness in a range of 0.002-0.04 inches. As shown, the elastomeric sheet 920 includes a first side 961 and a second side 962 disposed opposite to the first side 961. Further, the elastomeric sheet 930 includes a first side 970 and a second side 972 disposed opposite to the first side 970. Weld joints are formed in the first side 960 of the first elastomeric sheet 920 and the second side 972 of the second elastomeric sheet 930 in the grid pattern of weld joint regions 960.

Referring to FIG. 17, in one exemplary embodiment, in the grid pattern of weld joint regions 760, a thickness T16 of the first and second elastomeric sheets 920, 930 is greater than a thickness T17 of the first elastomeric sheet 920. Thus, if a tear occurs in the first elastomeric sheet 920 at an aperture 990, the adjacent weld joint region 960 having a greater thickness than the first elastomeric sheet 920 will tend to stop the tear from propagating across the adjacent weld joint region 960. In one exemplary embodiment, the thickness T17 of the first elastomeric sheet 920 is greater than a thickness T18 of the second elastomeric sheet 930. Of course, in an alternative embodiment, the thickness T17 could be substantially equal to the thickness T18.

Referring to FIGS. 16 and 18, in one exemplary embodiment, the plurality of apertures 940 extending through the second elastomeric sheet 930 are a plurality of polygon-shaped apertures. In particular, the plurality of apertures 940 are a plurality of rectangular-shaped apertures. An advantage of each rectangular-shaped aperture 940 is that this configuration disperses adjacent stresses to the weld joint regions 960 having a corresponding rectangular-shaped region disposed adjacent to the rectangular-shaped aperture 940 to reduce and/or prevent tear propagation. Of course, in an alternative embodiment, the plurality of apertures 940 could have other shapes, and/or alternating shapes and sizes.

In the exemplary embodiment, a size S5 across at least one aperture 940 is in a range of 2-20 millimeters. An advantage of an aperture 940 having a size S5 in a range of 2-20 millimeters is that the underlying layer 920 proximate to the aperture 940 can effectively surround a tooth extending through an aperture 990 punched in the dental dam 910. In an alternative embodiment, the aperture 940 could have other sizes, and/or alternating shapes and sizes depending on the desired application of the dental dam.

A further advantage of the configuration of the weld joint regions 960 is that tear propagation is further inhibited because the weld joint regions 960 are positioned such that a tear cannot easily propagate in a straight line across a central portion of the dental dam 910 without contacting at least one weld joint region 960. For example, a plane 1000 bisecting the first and second elastomeric sheets 920, 930 and extending through an outer side of the first elastomeric sheet 920 to an outer side of the second elastomeric sheet 930 will contact at least one weld joint region 960. Similarly, a plane 1010 bisecting the first and second elastomeric sheets 920, 930 and extending through an outer side of the first elastomeric sheet 920 to an outer side of the second elastomeric sheet 930 will contact at least one weld joint region 960. Still further, a plane 1020 bisecting the first and second elastomeric sheets 920, 930 and extending through an outer side of the first elastomeric sheet 920 to an outer side of the second elastomeric sheet 930 will contact at least one weld joint region 960.

Referring to FIGS. 16 and 18, in one exemplary manufacturing process, prior to the first and second elastomeric sheets 920, 930 being welded together to form the dental dam 910, the elastomeric sheets 920, 930 are distinct sheets. In one exemplary embodiment, the first elastomeric sheet 930 has the plurality of apertures 940 pre-cut therethrough.

In one exemplary embodiment, the elastomeric sheets 920, 930 have a substantially equal peripheral size to one another. Of course, in an alternative embodiment, the elastomeric sheets 920, 930 could have a different peripheral sizes from one another.

Referring to FIGS. 15, 16 and 18, the solvent welding device 850 can utilize a solvent that contacts the elastomeric sheets 920, 930 that are adjacently disposed to one another to weld the first and second elastomeric sheet 920, 930 to one another to form the dental dam 910.

Sixth Dental Dam Embodiment

Figure 19:
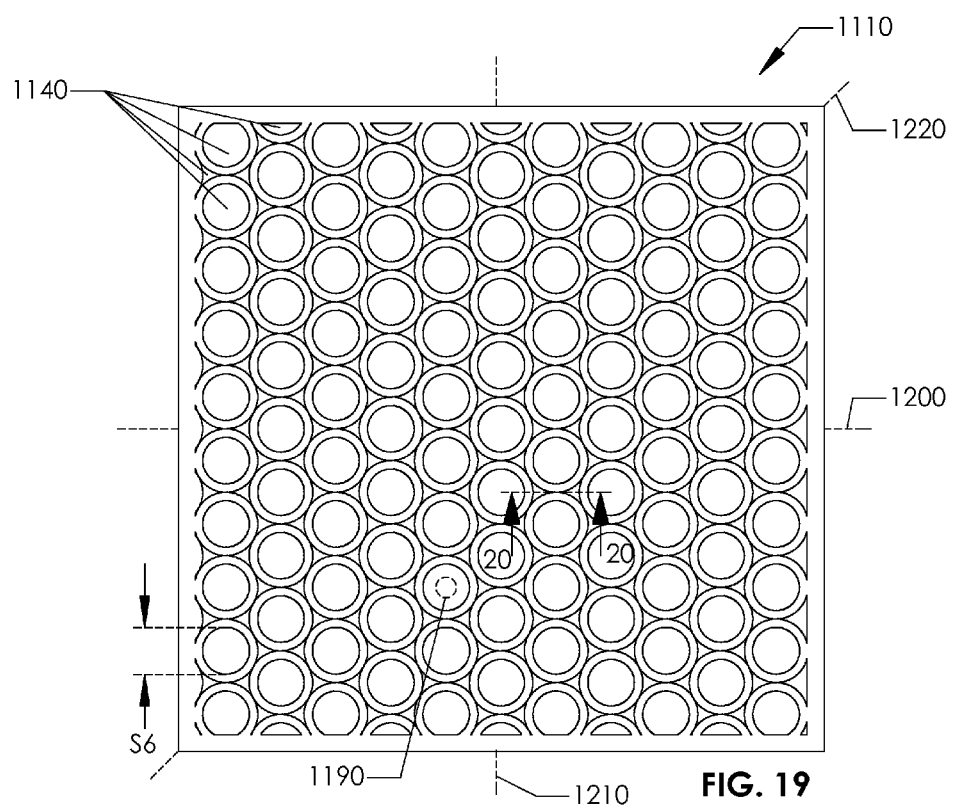
FIG. 19 is a schematic of a tear-resistant dental dam in accordance with another exemplary embodiment.
Figure 20:
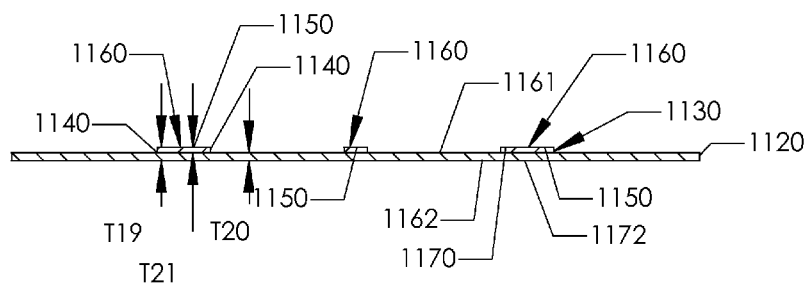
FIG. 20 is a cross-sectional schematic of a portion of the tear-resistant dental dam of FIG. 19.
Figure 21:
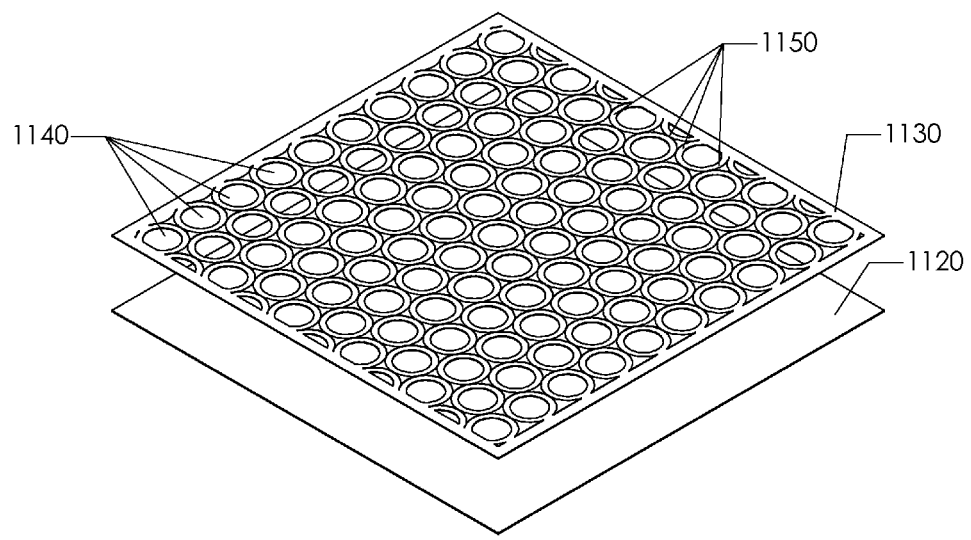
FIG. 21 is a schematic of first and second elastomeric sheets utilized to construct the tear-resistant dental dam of FIG. 19.

Referring to FIGS. 19-21, a tear-resistant dental dam 1110 in accordance with another exemplary embodiment is illustrated. The tear-resistant dental dam 1110 includes a first elastomeric sheet 1120 and a second elastomeric sheet 1130 disposed on the first elastomeric sheet 1120. The second elastomeric sheet 1130 has a plurality of apertures 1140 extending therethrough that define a grid pattern of elastomeric material 1150 of the second elastomeric sheet 1130. The grid pattern of elastomeric material 1150 is coupled to the first elastomeric sheet 1120 in a grid pattern of weld joint regions 1160. An advantage of the tear-resistant dental dam 1110 is that the dental dam 1110 utilizes the grid pattern of elastomeric material 1150 to reduce tear propagation in the dental dam 1110 as will be explained in greater detail below.

In one exemplary embodiment, the grid pattern of elastomeric material 1150 is welded to the first elastomeric sheet 1120 utilizing a solvent that forms weld joints in the first and second elastomeric sheets 1120, 1130. Of course, in an alternative embodiment, other types of welding methodologies disclosed herein.

In the exemplary embodiment, the first and second elastomeric sheets 1120, 1130 are constructed of a thermoplastic elastomer. For example, the first and second elastomeric sheets 1120, 1130 could be constructed of polyisoprene. Further, in one exemplary embodiment, the first and second elastomeric sheets 1120, 1130 are constructed of a non-latex elastomer. In an alternative embodiment, other elastomeric materials, such as latex for example, could be utilized to construct the first and second elastomeric sheets 1120, 1130. In the illustrated embodiment, the first and second elastomeric sheets 1120, 1130 have a similar peripheral size. In an alternative embodiment, the first and second elastomeric sheets 1120, 1130 could have a different peripheral size from one another. In one exemplary embodiment, each of the first and second elastomeric sheets 1120, 1130 have a thickness in a range of 0.002-0.04 inches. As shown, the elastomeric sheet 1120 includes a first side 1161 and a second side 1162 disposed opposite to the first side 1161. Further, the elastomeric sheet 1130 includes a first side 1170 and a second side 1172 disposed opposite to the first side 1170. Weld joints are formed in at least the first side 1161 of the first elastomeric sheet 1120 and the second side 1172 of the second elastomeric sheet 1130 in the grid pattern of weld joint regions 1160.

Referring to FIG. 20, in one exemplary embodiment, in the grid pattern of weld joint regions 1160 a thickness T19 of the first and second elastomeric sheets 1120, 1130 is greater than a thickness T20 of the first elastomeric sheet 1120. Thus, if a tear occurs in the first elastomeric sheet 1120 at an aperture 1190, the adjacent weld joint region 1160 having a greater thickness than the first elastomeric sheet 1120 will tend to stop the tear from propagating across the adjacent weld joint region 1160. In one exemplary embodiment, the thickness T20 of the first elastomeric sheet 1120 is greater than a thickness T21 of the second elastomeric sheet 1130. Of course, in an alternative embodiment, the thickness T20 could be substantially equal to the thickness T21.

Referring to FIGS. 19 and 21, in one exemplary embodiment, the plurality of apertures 1140 extending through the second elastomeric sheet 1130 are a plurality of circular-shaped apertures. An advantage of each circular-shaped aperture 1140 is that this configuration disperses adjacent stresses to the weld joint regions 1160 having a corresponding circular-shaped region disposed adjacent to the circular-shaped aperture 1140 to reduce and/or prevent tear propagation. Of course, in an alternative embodiment, the plurality of apertures 1140 could have other shapes, or alternating shapes and sizes.

In the exemplary embodiment, a size S6 across at least one aperture 1140 is in a range of 2-20 millimeters. An advantage of an aperture 1140 having a size S6 in a range of 2-20 millimeters is that the underlying layer 1120 proximate to the aperture 1140 can effectively surround a tooth extending through an aperture 1190 punched in the dental dam 1110. In an alternative embodiment, the aperture 1140 could have other sizes, and/or alternating shapes and sizes depending on the desired application of the dental dam.

A further advantage of the configuration of the weld joint regions 1160 is that tear propagation is further inhibited because the weld joint regions 1160 are positioned such that a tear cannot propagate in a straight line across a central portion of the dental dam 1110 without contacting at least one weld joint region 1160. For example, a plane 1200 bisecting the first and second elastomeric sheets 1120, 1130 and extending through an outer side of the first elastomeric sheet 1120 to an outer side of the second elastomeric sheet 1130 will contact at least one weld joint region 1160. Similarly, a plane 1210 bisecting the first and second elastomeric sheets 1120, 1130 and extending through an outer side of the first elastomeric sheet 1120 to an outer side of the second elastomeric sheet 1130 will contact at least one weld joint region 1160. Still further, a plane 1220 bisecting the first and second elastomeric sheets 1120, 1130 and extending through an outer side of the first elastomeric sheet 1120 to an outer side of the second elastomeric sheet 1130 will contact at least one weld joint region 1160.

Referring to FIG. 21, in an exemplary manufacturing process, prior to the first and second elastomeric sheets 1120, 1130 being welded together to form the dental dam 1110, the elastomeric sheets 1120, 1130 are distinct sheets. In one exemplary embodiment, the first elastomeric sheet 1130 has the plurality of apertures 1140 pre-cut therethrough. In one exemplary embodiment, the elastomeric sheets 1120, 1130 have a substantially equal peripheral size to one another. Of course, in an alternative embodiment, the elastomeric sheets 1120, 1130 could have a different peripheral sizes from one another.

Referring to FIGS. 15, 19 and 21, the solvent welding device 850 can utilize a solvent that contacts the elastomeric sheets 1120, 1130 that are adjacently disposed to one another to weld the first and second elastomeric sheet 1120, 1130 to one another to form the dental dam 1110.

Seventh Dental Dam Embodiment

Figure 22:
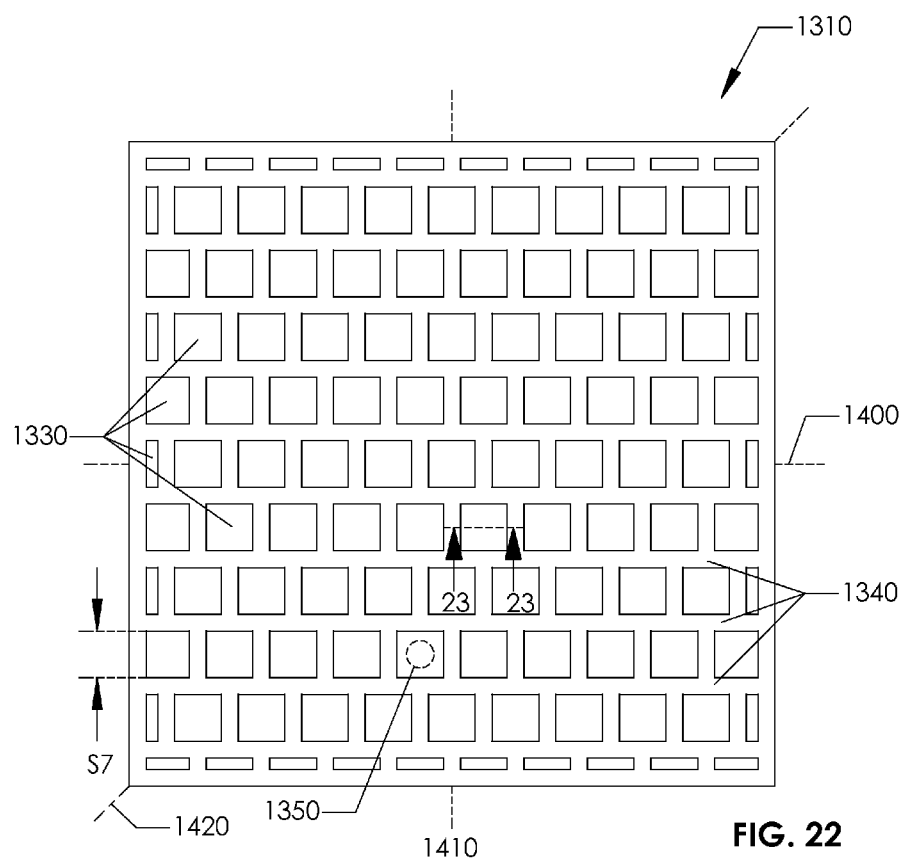
FIG. 22 is a schematic of a tear-resistant dental dam in accordance with another exemplary embodiment.
Figure 23:
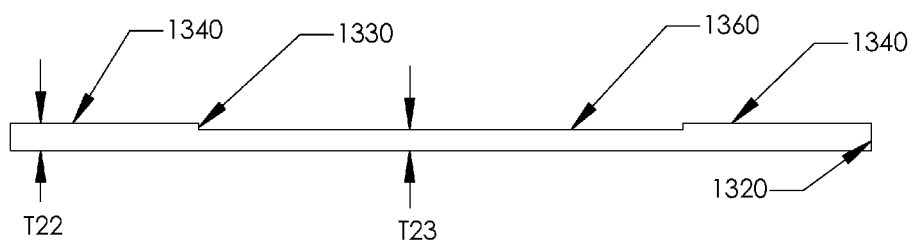
FIG. 23 is a cross-sectional schematic of a portion of the tear-resistant dental dam of FIG. 22.

Referring to FIGS. 22-23, a tear-resistant dental dam 1310 in accordance with another exemplary embodiment is illustrated. The tear-resistant dental dam 1310 includes an elastomeric sheet 1320. The elastomeric sheet 1320 has a plurality of pocket regions 1330 defining a grid pattern of elastomeric material 1340.

In the exemplary embodiment, the elastomeric sheet 1320 is constructed of a thermoplastic elastomer. For example, the elastomeric sheet 1320 could be constructed of polyisoprene. Further, in one exemplary embodiment, the elastomeric sheet 1320 is constructed of a non-latex elastomer. In an alternative embodiment, other elastomeric materials, such as latex for example, could be utilized for the elastomeric sheet 1320.

Referring to FIG. 23, in one exemplary embodiment, a thickness T23 of the elastomeric sheet 1320 in the grid pattern of elastomeric material 1340 is greater than a thickness T23 of the elastomeric portion 1360 of the elastomeric sheet 1320 underlying the pocket region 1330. Thus, if a tear occurs in the elastomeric sheet 1320 at an aperture 1350 in the elastomeric portion 1360, the adjacent grid pattern of elastomeric material 1340 having a greater thickness than the elastomeric portion 1360 will tend to stop the tear from propagating across the adjacent grid pattern of elastomeric material 1340.

In one exemplary embodiment, the plurality of pocket regions 1330 extending into the elastomeric sheet 1320 are a plurality of rectangular-shaped pocket regions. An advantage of each rectangular-shaped pocket regions 1330 is that this configuration disperses adjacent stresses to the grid pattern of elastomeric material 1340 having a corresponding rectangular shape to reduce and/or prevent tear propagation. Of course, in an alternative embodiment, the plurality of pocket regions 1330 could have other shapes such as a hexagonal shape or a circular shape for example. In another alternative embodiment, the plurality of pocket regions 1330 could have alternating shapes and/or sizes to accommodate different applications of dental procedures.

In the exemplary embodiment, a size S7 across at least one pocket region 1330 is in a range of 2-20 millimeters. An advantage of a pocket region 1330 having a size S7 in a range of 2-20 millimeters is that the underlying elastomeric portion 1360 proximate to the aperture 1350 can effectively surround a tooth extending through an aperture 1350 punched in the dental dam 1310. In an alternative embodiment, the pocket region 1330 could have other sizes depending on the desired application of the dental dam. In another alternative embodiment, the plurality of pocket regions 1330 could have alternating shapes and/or sizes to accommodate different applications of dental procedures.

A further advantage of the configuration of the grid pattern of elastomeric material 1350 is that tear propagation is further inhibited because the grid pattern of elastomeric material 1350 is positioned such that a tear cannot propagate in a straight line across a central portion of the dental dam 1310 without contacting at least a portion of the grid pattern of elastomeric material 1350. For example, a plane 1400 bisecting the elastomeric sheet 1320 will contact at least a portion of the grid pattern of elastomeric material 1350. Similarly, a plane 1410 bisecting the elastomeric sheet 1320 will contact at least a portion of the grid pattern of elastomeric material 1350. Still further, a plane 1420 bisecting the elastomeric sheet 1320 will contact at least a portion of the grid pattern of elastomeric material 1350.

Referring to FIGS. 5-7, 19 and 20, the dental dam 1310 can be constructed utilizing at least one of the hot plate welding device 230, the ultrasonic welding device 240, and the radio-frequency welding device 250.

The dental dams described herein provide a substantial advantage over other dental dams. In particular, the dental dams provide a technical effect of utilizing a grid pattern of weld joint regions and a plurality of unwelded regions of first and second elastomeric sheets to reduce tear propagation in the dental dams.

While the claimed invention has been described in detail in connection with only a limited number of embodiments, it should be readily understood that the invention is not limited to such disclosed embodiments. Rather, the claimed invention can be modified to incorporate any number of variations, alterations, substitutions or equivalent arrangements not heretofore described, but which are commensurate with the spirit and scope of the invention. Additionally, while various embodiments of the claimed invention have been described, it is to be understood that aspects of the invention may include only some of the described embodiments. Accordingly, the claimed invention is not to be seen as limited by the foregoing description.

What is claimed is:

1. A tear-resistant dental dam, comprising:
a first thermoplastic elastomeric sheet; and
a second thermoplastic elastomeric sheet having an entire first side disposed directly on and contacting the first thermoplastic elastomeric sheet, the first and second thermoplastic elastomeric sheets having a grid pattern of weld joint regions that couple together the first and second thermoplastic elastomeric sheets, the grid pattern of weld joint regions defining a plurality of unwelded regions of the first and second thermoplastic elastomeric sheets, the first side of the second thermoplastic elastomeric sheet is not welded to the first thermoplastic elastomeric sheet in the plurality of unwelded regions, the first side of the second thermoplastic elastomeric sheet contacting and covering the first thermoplastic elastomeric sheet in the plurality of unwelded regions, a combined thickness of the first and second thermoplastic elastomeric sheets in each unwelded region of the plurality of unwelded regions being greater than a combined thickness of the first and second thermoplastic elastomeric sheets in the grid pattern of weld joint regions.

2. The tear-resistant dental dam of claim 1, wherein a thickness of the first and second thermoplastic elastomeric sheets in the grid pattern of weld joint regions is greater than a thickness of the first thermoplastic elastomeric sheet in an unwelded region of the plurality of unwelded regions.

3. The tear-resistant dental dam of claim 2, wherein the thickness of the first and second thermoplastic elastomeric sheets in the grid pattern of weld joint regions is greater than a thickness of the second thermoplastic elastomeric sheet in an unwelded region of the plurality of unwelded regions.

4. The tear-resistant dental dam of claim 1, wherein a plane bisecting the first and second thermoplastic elastomeric sheets and extending through an outer side of the first thermoplastic elastomeric sheet to an outer side of the second thermoplastic elastomeric sheet will contact at least one unwelded region of the plurality of unwelded regions and at least a portion of the grid pattern of weld joint regions.

5. The tear-resistant dental dam of claim 1, wherein at least one unwelded region of the plurality of unwelded regions is a polygon-shaped unwelded region.

6. The tear-resistant dental dam of claim 5, wherein the polygon-shaped unwelded region is a rectangular-shaped unwelded region.

7. The tear-resistant dental dam of claim 5, wherein the polygon-shaped unwelded region is a hexagonal-shaped unwelded region.

8. The tear-resistant dental dam of claim 1, wherein at least one unwelded region of the plurality of unwelded regions is a circular-shaped unwelded region.

9. The tear-resistant dental dam of claim 1, wherein a size across at least one unwelded region of the plurality of unwelded regions is in a range of 2-20 millimeters.

10. The tear-resistant dental dam of claim 1, wherein an outer periphery of the first thermoplastic elastomeric sheet and an outer periphery of the second thermoplastic elastomeric sheet have a peripheral weld joint region such that the first and second thermoplastic elastomeric sheets are further coupled together at the peripheral weld joint region.

11. The tear-resistant dental dam of claim 1, wherein the first and second thermoplastic elastomeric sheets have an aperture extending through a first unwelded region of the plurality of unwelded regions, the aperture being sized to receive a tooth therethrough.

12. The tear-resistant dental dam of claim 1, wherein the first and thermoplastic elastomeric sheets are each constructed of polyisoprene.

13. The tear-resistant dental dam of claim 1, wherein the first side of the second thermoplastic elastomeric sheet completely covers and directly contacts the first thermoplastic elastomeric sheet in the plurality of unwelded regions.

14. A tear-resistant dental dam, comprising:
a thermoplastic elastomeric sheet having a plurality of pocket regions defining a grid pattern of elastomeric material, a thickness of a portion of the elastomeric sheet underlying the plurality of pocket regions being greater than two-thirds of a thickness of the grid pattern of elastomeric material; at least first and second pocket regions of the plurality of pocket regions each having a width less than one-third of a width of a third pocket region of the plurality of pocket regions.

15. A tear-resistant dental dam, comprising:
a first thermoplastic elastomeric sheet; and
a second thermoplastic elastomeric sheet having an entire first side disposed directly on and contacting the first thermoplastic elastomeric sheet, the first and second thermoplastic elastomeric sheets having a grid pattern of weld joint regions that couple together the first and second thermoplastic elastomeric sheets, the grid pattern of weld joint regions defining a plurality of unwelded regions of the first and second thermoplastic elastomeric sheets, the first side of the second thermoplastic elastomeric sheet is not coupled to the first thermoplastic elastomeric sheet in the plurality of unwelded regions, the first side of the second thermoplastic elastomeric sheet contacting and covering the first thermoplastic elastomeric sheet in the plurality of unwelded regions, a combined thickness of the first and second thermoplastic elastomeric sheets in each unwelded region of the plurality of unwelded regions being greater than a combined thickness of the first and second thermoplastic elastomeric sheets in the grid pattern of weld joint regions.

16. The tear-resistant dental dam of claim 15, wherein the first side of the second thermoplastic elastomeric sheet completely covers and directly contacts the first thermoplastic elastomeric sheet in the plurality of unwelded regions.

\* \* \* \* \*